(12) United States Patent
Bilen-Rosas et al.

(10) Patent No.: US 12,298,275 B2
(45) Date of Patent: May 13, 2025

(54) SYSTEM AND METHOD FOR MEASURING PRESSURE USING ULTRASOUND

(71) Applicant: Wisconsin Alumni Research Foundation, Madison, WI (US)

(72) Inventors: Guelay Bilen-Rosas, Middleton, WI (US); Humberto Gerardo Rosas, Middleton, WI (US); Quinton White Guerrero, Madison, WI (US); Irene May Lin Ong, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 17/228,376

(22) Filed: Apr. 12, 2021

(65) Prior Publication Data

US 2021/0318268 A1    Oct. 14, 2021

Related U.S. Application Data

(60) Provisional application No. 63/008,164, filed on Apr. 10, 2020.

(51) Int. Cl.
*G01N 29/024* (2006.01)
*A61B 5/00* (2006.01)

(52) U.S. Cl.
CPC ......... *G01N 29/024* (2013.01); *A61B 5/7415* (2013.01); *G01N 2291/017* (2013.01); *G01N 2291/02466* (2013.01); *G01N 2291/02836* (2013.01); *G01N 2291/02872* (2013.01)

(58) Field of Classification Search
CPC .......... G01N 29/024; G01N 2291/017; G01N 2291/02466; G01N 2291/02836; G01N 2291/02872; A61B 5/745
USPC .......................................................... 73/584
See application file for complete search history.

(56) References Cited

U.S. PATENT DOCUMENTS

| | | | |
|---|---|---|---|
| 2009/0216127 A1* | 8/2009 | Gavriely | A61B 7/003 600/453 |
| 2014/0039313 A1* | 2/2014 | Palti | A61B 8/5223 600/438 |
| 2019/0167227 A1* | 6/2019 | Bilen-Rosas | A61B 5/7405 |

FOREIGN PATENT DOCUMENTS

WO    WO-2018053493 A1 *    3/2018    ............. A61B 5/087

* cited by examiner

*Primary Examiner* — John Fitzgerald
*Assistant Examiner* — Rose M Miller
(74) *Attorney, Agent, or Firm* — Quarles & Brady, LLP

(57) ABSTRACT

Pressure and pressure or displacement variations are measured in a media, such as a fluid (e.g., air, other gases, or other liquid fluids), using ultrasound. The pressure may be sound pressure (e.g., acoustic pressure), pseudo-sound pressure (e.g., hydrodynamic pressure), displacement, and so on. By measuring pressure or displacement, the flow in the fluid can be measured, estimated, parameterized, or otherwise quantified. In this way, measurements of pressure (e.g., acoustic pressure, hydrodynamic pressure) or displacement can be correlated or otherwise converted into a measurement of flow. The pressure measurements can also be converted into audio signals that can be played back to a user.

18 Claims, 4 Drawing Sheets

SYSTEM AND METHOD FOR MEASURING PRESSURE USING ULTRASOUND

CROSS-REFERENCE TO RELATED APPLICATIONS

This application claims the benefit of U.S. Provisional Patent Application Ser. No. 63/008,164 filed on Apr. 10, 2020 and entitled "SYSTEM AND METHOD FOR MEASURING PRESSURE USING ULTRASOUND", the content of which is incorporated herein by reference in its entirety.

BACKGROUND

Acoustic pressure recording devices currently cannot measure acoustic pressure occurring inside the human body. Further, current acoustic pressure recording devices use an acoustic pressure sensor that is in direct contact with the acoustic pressure being sensed (i.e., in air or a media). It would be advantageous, then, to have a system and method capable of measuring acoustic pressure, acoustic displacement, or any acoustic pressure variations without requiring direct contact with the region where the acoustic disturbance is being sensed.

SUMMARY OF THE DISCLOSURE

The present disclosure addresses the aforementioned drawbacks by providing a method for measuring acoustic pressure or displacement using an ultrasound system. The method includes acquiring ultrasound data from a region-of-interest using an ultrasound system by generating with the ultrasound system one or more transmitted ultrasound waves that, when interacting with vibrations caused at an interface between a first and second medium in the region-of-interest by displacement or one or more pressure waves propagating in the first medium, generate one or more reflected ultrasound waves that encode the vibrations caused by the displacement or one or more pressure waves. The ultrasound data are accessed with a computer system in order to process the ultrasound data, generating output as pressure or displacement data indicative of pressure or displacement measurements associated with the one or more pressure waves or displacements propagating in the first medium. The pressure or displacement data are then output to a user using the computer system.

It is another aspect of the present disclosure to provide an ultrasound microphone. The ultrasound microphone includes an ultrasound transducer and a controller in communication with the ultrasound transducer. The controller is programmed to cause the ultrasound transducer to transmit one or more ultrasound waves; to receive ultrasound data from the ultrasound transducer; and to convert the ultrasound data to pressure or displacement data. The ultrasound data indicate an interaction between the one or more ultrasound waves and an interface between a first and second medium (e.g., a fluid-media interface) that is vibrating in response to one or more pressure waves propagating in the fluid, and the pressure data are representative of pressure measurements associated with the one or more pressure waves propagating in the fluid.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
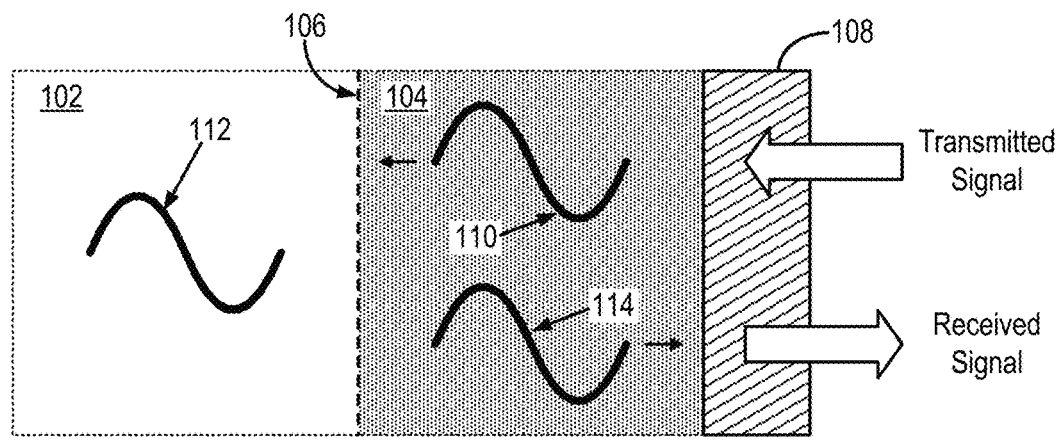
FIG. 1 is a schematic representation of measuring pressure variations at an interface (e.g., a fluid-media interface) using ultrasound.

Described here are systems and methods for measuring pressure and pressure variations in a media, which may be a fluid (e.g., air or other gases or fluids), using ultrasound. The pressure may be sound pressure (e.g., acoustic pressure), pseudo-sound pressure (e.g., hydrodynamic pressure), and so on. By measuring pressure, the flow in the media can be measured, estimated, parameterized, or otherwise quantified. In this way, measurements of pressure (e.g., acoustic pressure, hydrodynamic pressure) can be correlated or otherwise converted into a measurement of flow. In some implementations, particle velocity can also be measured by measuring displacements in the media.

The systems and methods described in the present disclosure can measure the turbulence boundary layer caused by airflow at an interface layer. Unlike traditional methods for measuring pressure, the systems and methods described in the present disclosure do not need to be in direct physical contact with the interface layer. Rather, ultrasound can be transmitted to the interface layer and the received ultrasound echo data can be processed to quantify or otherwise parameterize the pressure. Further, whereas conventional techniques seek to minimize turbulent flow, the systems and methods described in the present disclosure are instead capable of measuring turbulent flow.

Advantageously, ambient and environmental noise is not captured using this technique, thereby providing an additional improvement over conventional acoustic pressure measurement systems and methods. In this way, the systems and methods described in the present disclosure are capable of measuring lower frequency pressures than can be reliably measured with conventional acoustic pressure sensors (e.g., acoustic microphones).

As a non-limiting example, during the respiratory cycle, the passage of air forms a laryngeal jet resulting in turbulent flow through the larynx and trachea. The interface layer between the air and surrounding tissues (e.g., laryngeal wall, tracheal wall) is a turbulent boundary layer of flow. The degree of turbulent flow is dependent on air velocity and volume. Wall pressure fluctuations produced by the turbulent boundary layer create vibration, or other motion, of the trachea (or larynx), which generates a pressure distribution (e.g., a pseudo-sound). This pressure can be detected, recorded, and otherwise measured using ultrasound (e.g., using pulsed-wave Doppler ultrasound) imaging at the air-wall interface.

In addition to measuring pressure at or near the air-wall interface in the trachea or larynx, the systems and methods described in the present disclosure can be used in other clinical and non-destructive testing applications. For instance, the systems and methods described in the present disclosure can be used in aerospace applications, whereby pressure induced turbulent flow over wings can be measured to provide quantitative information useful for refining the aircraft wing, measuring the efficiency of the wing design, detecting structural weaknesses in the wing, and so on. Similarly, the systems and methods described in the present disclosure can be used for other non-destructive testing and flow monitoring applications, such as in turbines and duct work. Furthermore, this method is not limited to measuring pressure in air, but can also be used to record or otherwise measure underwater sounds (e.g., as may be used for tracking ships, submarines, or animals in the ocean).

The general process implemented by the systems and methods described in the present disclosure is illustrated in FIG. 1. Here, a first medium 102 is in fluid communication with a second medium 104 at an interface boundary layer 106. As noted above, the first medium is preferably a fluid medium, such as air or other gases or liquid fluids, but in some instances may be a non-fluid medium, such as a membrane. The second medium 104 may be a tissue (e.g., laryngeal wall tissue, tracheal wall tissue) or other non-biological material (e.g., metal, ceramic, plastic). An ultrasound transducer 108 is placed into contact with the second medium. In some instances, such as in biological applications, additional media may be present between the ultrasound transducer 108 and the second medium 104. As an example, when the second medium 104 includes tissues associated with the tracheal or laryngeal wall of a subject, these additional media may include other tissues such as skin, muscle, and fat.

An acoustic coupling media (e.g., an acoustic coupling gel) may be arranged between the ultrasound transducer 108 and the second medium 104. For example, an acoustic coupling media may be applied to the skin surface of a subject.

The ultrasound transducer 108 receives a transmitted signal and in response generates an ultrasound wave 110, or other ultrasound energy, that propagates through the second medium 104 towards the boundary layer 106. At the boundary layer 106, the transmitted ultrasound wave 110 interacts with or otherwise detects vibrations at the boundary layer 106 that are caused by pressure waves 112 propagating in the first medium 102. These pressure waves 112 may be, for example, acoustic pressure waves (e.g., sound waves), hydrodynamic or aerodynamic pressure waves (e.g., pseudo-sound waves), displacement, or the like. The pressure waves 112 are generally indicative of turbulent flow, which causes vibration or other motion at the boundary layer 106. In response to these interactions, a reflected ultrasound wave 114, or other ultrasound energy, is generated and propagates through the second medium 104 back towards the ultrasound transducer 108. These reflected ultrasound waves 114 are measured or otherwise detected by the ultrasound transducer 108 and converted to ultrasound data. As one example, the ultrasound data may be Doppler ultrasound data.

The ultrasound data are then communicated to or otherwise accessed by a computer system, where they are processed to measure or otherwise quantify the pressure or displacement in the first medium 102. Additionally or alternatively, the measured pressure or displacement can be further parameterized by estimating parameters such as volumetric flow, flow velocity, vorticity, Reynold's number, and so on.

In pulsed-wave Doppler ("PW"), a series of long-duration ultrasound pulses are used to compute a velocity spectrum of moving objects in a region-of-interest. Similar to conventional B-mode ultrasound, PW Doppler uses a pulse-echo sequence: the transmission and reception of an ultrasound pulse and its echo using the same transducer. The primary difference between B-mode and PW Doppler is that the number of ultrasound pulses used to perform PW Doppler is often many times greater than B-mode techniques.

For each ultrasound pulse, the ultrasound wave will experience a slightly different phase shift; therefore, in some instances the ultrasound pulse can be sampled many times to adequately characterize the frequency at which the phase shift occurs. Most often, the frequency of the phase shifts is computed through the Fourier transform of the echo signal power as it changes from pulse-to-pulse. To more precisely define the time-frame of "pulse-to-pulse" change in echo signal power, the PW Doppler pulses are said to occur in "slow-time," or the time relative to the pulse repetition frequency ("PRF").

Using this vernacular, it can be said that the PW Doppler signal is the Fourier transform of the echo signal power as a function of slow-time. Objects moving in the PW Doppler region-of-interest cause the echo signal power to vary as a function of slow-time. If the objects moving in the region-of-interest move at a single speed, the frequency of the variation of echo signal power as a function of slow-time may occur at one distinct frequency. One way to characterize this is by computing the power spectrum (or squared modulus of the Fourier transform) of the echo signal power as a function of slow-time.

The PW Doppler power spectrum can indicate the power of each frequency at which the echo signal power varies as a function of slow-time. Each frequency of phase shift corresponds to a velocity, depending on the speed of sound in the media, the frequency of the acoustic pulse, and the PRF.

It may be desirable to determine if the objects in the region-of-interest are moving towards or away from the direction at which the ultrasound pulse is traveling. In these instances, by taking the Hilbert transform of the ultrasound echo signal along the "fast-time" dimension (e.g., the axial, depth, or pulse's propagation direction), before Fourier transformation in slow-time, the direction of motion relative to the pulse's propagation direction can be determined. The imaginary component of the Hilbert transform allows the computation of "negative" and "positive" frequency components using the Fourier transform, or, determination of the direction of the phase change as a function of slow-time.

As an example, the systems and methods described in the present disclosure can use pulsed-wave Doppler focused on an air-media interface to measure sound waves/acoustic pressure propagating in air. These measurements are can be correlated with reference data, which may include traditional sound waves measured using standard calibrated electrical equipment. Unlike a traditional electronic microphone, which converts sound pressure to an electrical signal via direct interaction of the acoustic pressure with a sensing element, the ultrasound pulsed-wave Doppler signal is produced by the interaction of the transmitted ultrasound waves with the acoustic sound/acoustic pressure/acoustic displacement traveling at the air-media interface (e.g., the interface with a wall of a tube and air).

As one implementation of the preceding example, power spectra of the ultrasound Doppler signal can be measured at the air-media interface between the tracheal wall and the air inside the trachea. At this interface, during breathing, breath sounds can be measured and recorded throughout a subject's respiration. It is a discovery of the present disclosure that, quantitatively, the ultrasound Doppler signal power is linearly related to the logarithm of the volumetric flow rate, indicating a link between aerodynamic pressure and the measured ultrasound Doppler signal.

In some instances, a measurement modality other than ultrasound can be used to measure the flow and/or pressure at an interface layer, from which pressure measurements can be estimated as described in the present disclosure. As one example, other acoustic-based measurement techniques could be used, such as Doppler radar. In some other example, electromagnetic wave-based techniques could be used, such as using laser-based measurements, infrared imaging, optical imaging, radio-wave-based measurements, infrared thermography, optoelectronics, and so on. In other examples, thermal measurements, magnetometry, and/or pressure manometry could be used to acquire measurements from which pressure can be estimated according to the methods described in the present disclosure.

Figure 2:
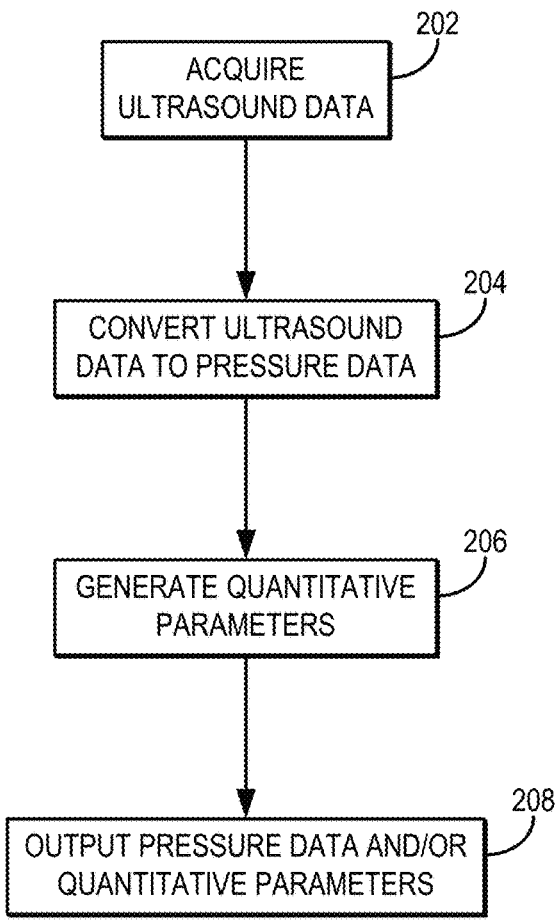
FIG. 2 is a flowchart setting forth the steps of an example method for measuring pressure or pressure variations at an interface (e.g., a fluid-media interface) using ultrasound.

Referring now to FIG. 2, a flowchart is illustrated as setting forth the steps of an example method for measuring pressure in a region-of-interest (e.g., at an interface layer) using ultrasound.

The method includes acquiring ultrasound data from a region-of-interest using an ultrasound system, as indicated at step 202. The ultrasound data may be acquired using a pulsed-wave Doppler technique. In some other embodiments, continuous wave Doppler techniques can be implemented. The region-of-interest includes a region where turbulent flow is occurring. In general, the region-of-interest can include an interface or boundary layer between two different media. As described above, one of the media may be a fluid, such as air, other gases, or other liquid fluids, in which flow (e.g., turbulent flow, laminar flow) is occurring. The other media may be tissue (e.g., tissues associated with a laryngeal wall, tracheal wall) or any other suitable material that may be in fluid communication with the fluid media.

The ultrasound data are then processed to generate pressure data representative of pressure measurements from the fluid media, as indicated at step 204. The pressure data indicate a pressure distribution at the interface or boundary layer. This is in contrast to conventional acoustic pressure measurement techniques, which measure acoustic pressures at the point location of the pressure sensor. In some instances, the pressure data can be generated by correlating or otherwise comparing the ultrasound data with reference data. As one example, the reference data may include pressure data acquired from similar air-media interfaces using non-ultrasound based techniques, such as an electronic microphone. As another example, the reference data may include empirically determined data that correlates ultrasound data to pressure measurements. Such empirically determined data may include data plots or functions that enable conversion of the ultrasound data to the pressure data. As one non-limiting example, the reference data may include empirically determined linear functions or relationships between ultrasound and pressure data.

In some instances, comparing the ultrasound data to reference data can include inputting the ultrasound data to a machine learning algorithm, generating output as the pressure or displacement data. The machine learning algorithm may be a deep learning model, or other suitable machine learning algorithm, that was trained with reference data. For example, a deep learning model, supervised machine learning algorithm, or other suitable machine learning algorithm, can be trained on reference data to convert or otherwise correlate ultrasound data with pressure measurements. The trained machine learning algorithm can include or otherwise implement a support vector machine ("SVM"), a random forest, a conditional random field, a hidden Markov model, a neural network, and other deep learning models or algorithms.

Additionally or alternatively, the pressure or displacement data may be further processed to generate one or more quantitative parameters or parameter maps, as indicated at step 206. As one example, flow can be estimated from the measured pressure data. For instance, volumetric flow rate can be quantified using the following relationship:

$$Q = \frac{\pi r^4 \Delta AP}{8\eta L}; \qquad (1)$$

where Q is the volumetric flow rate, r is the radius of the tube through which the fluid (e.g., air or other fluid) is flowing, $\Delta AP$ is the measured aerodynamic pressure (e.g., acoustic pressure, hydrodynamic pressure), $\eta$ is the viscosity of the fluid (e.g., air or other fluid), and L is the length of the tube through which the fluid (e.g., air or other fluid) is flowing. Other parameters can also be estimated from the measured pressure data, including flow velocity, vorticity, and Reynold's number (e.g., quantifying turbulence).

The pressure data, quantitative parameters, parametric maps, or combinations thereof can be output to a user or stored for later use, as indicated at step 208. In some instances, the pressure data can be output to a user by first converting the pressure data to an acoustic signal that is then output to the user as an audible sound. In these instances, the pressure or displacement variations in the media at the interface (e.g., fluid as a fluid-media interface) are encoded into the ultrasound data, converted first to pressure data representative of the pressure variations, and then converted into sounds that can be played back to the user. In this way, the ultrasound system can be used as a microphone that is capable of measuring, recording, and playing back sounds that are occurring in the substrate media.

Additionally or alternatively, the output can include a visual depiction of quantitative parameters or parameter maps. For instance, the output can depict a spatial distribution of one or more quantitative parameters within the region-of-interest.

The systems and methods described in the present disclosure have numerous applications in addition to evaluating laryngeal and glottal pathologies for phonation and/or voice assessments. As one non-limiting example, vascular wall pathology could be evaluated by measuring and predicting wall pressure changes due to a disease process. In these instances, the interface would be between blood and the vessel wall.

As another non-limiting example, the systems and methods described in the present disclosure can provide for a dynamic microphone. The sensitivity of ultrasound Doppler to different frequencies of acoustic pressure is dependent on the frequency of the ultrasound transmit pulse. All electronic microphones have a set frequency sensitivity to acoustic pressure that is determined by the physical mechanism that converts pressure to electricity. An ultrasound microphone implementing the techniques described in the present disclosure can be programmed to dynamically change its acoustic pressure sensitivity by changing the frequency of the transmitted ultrasound pulse.

Figure 3:
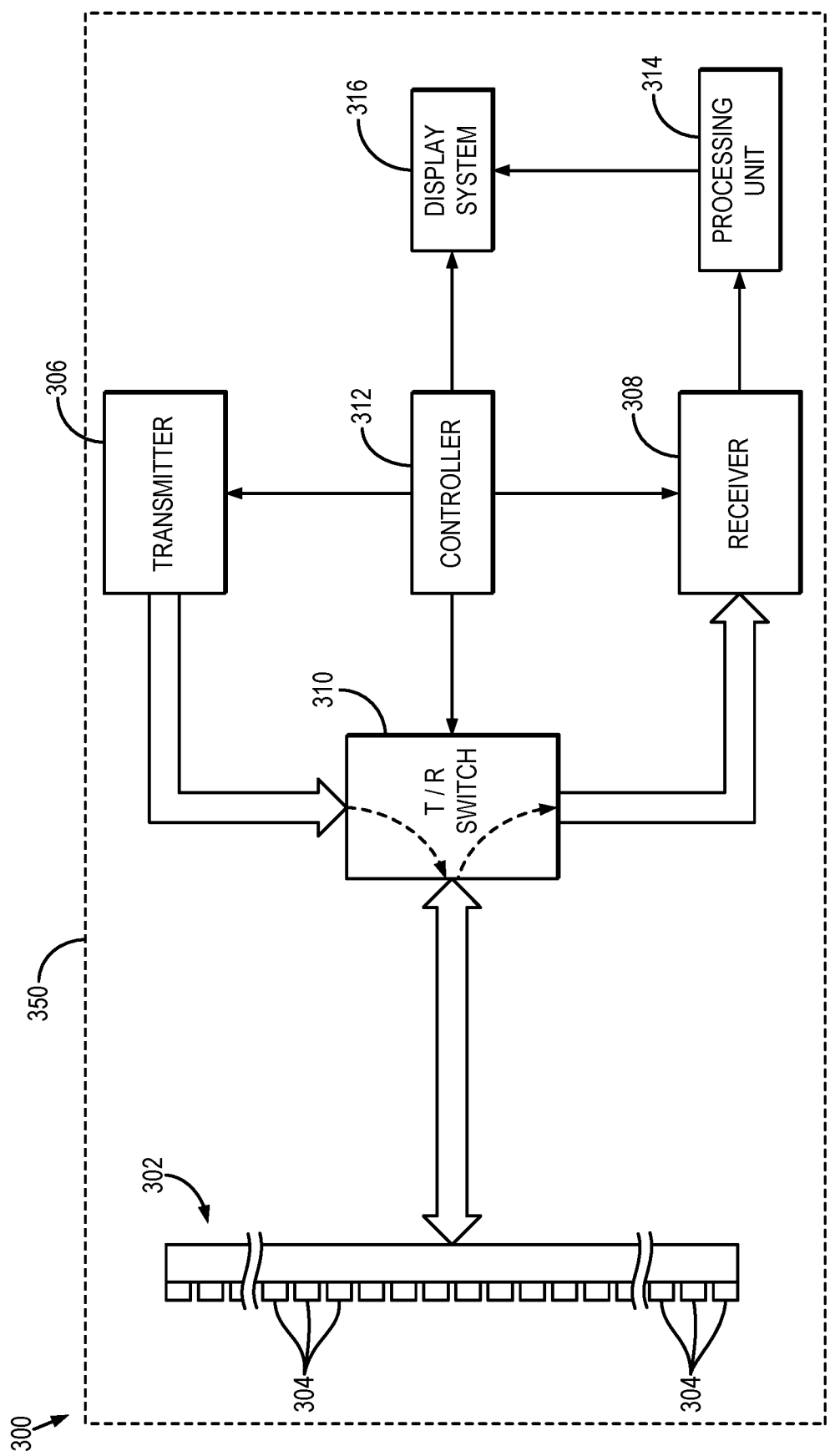
FIG. 3 is a block diagram of an example ultrasound system that can implement the methods described in the present disclosure.

As another non-limiting example, the systems and methods described in the present disclosure can provide for a water-proof microphone. Because an ultrasound pulse is used to sample sound (e.g., by measuring acoustic pressure variations associated with a sound), an ultrasound-based microphone system can be encased in a waterproof housing 350 (as shown in FIG. 3), rendering the system waterproof. Such a system can be capable of measuring sounds in water.

As mentioned above, in another non-limiting example, the systems and methods described in the present disclosure can be used to non-invasively monitor air-flow in ducts. Using an acoustic source, it can be possible to measure the air-flow in a duct by measuring the change in the acoustic signal along the length of the duct. Ultrasound would be non-invasive and could be installed or otherwise implemented on any metallic duct.

As another non-limiting example, an ultrasound microphone system implementing the techniques described in the present disclosure could be used to hear on the other side of a wall. Because the ultrasound pulse itself acts as a "microphone" that measures and encodes the vibrations caused by pressure variations in a fluid, sounds can be recorded from fluid-media interface locations to which an ultrasound pulse can be transmitted. In this way, an ultrasound transducer can be used to measure, and therefore record, sounds that are generated on the other side of a wall.

As still another non-limiting example, the systems and methods described in the present disclosure can be used to monitor turbulence without microphones. Conventional techniques to measure turbulence in aerospace and automotive research is to drill a hole into metal or plastic pieces and install a set of microphones. The process of installing the microphone often perturbs the turbulence that the researchers are trying to measure. An ultrasound-based microphone enables non-invasive measurement of turbulence. Using arrays of ultrasound transducers (or transducer elements), an ultrasound pulse can be swept along a spatial extent (e.g., a length of tube or other object), allowing for non-conventional measurements of turbulence.

FIG. 3 illustrates an example of an ultrasound system 300 that can implement the methods described in the present disclosure. The ultrasound system 300 includes a transducer array 302 that includes a plurality of separately driven transducer elements 304. The transducer array 302 can include any suitable ultrasound transducer array, including linear arrays, curved arrays, phased arrays, and so on. Similarly, the transducer array 302 can include a 1D transducer, a 1.5D transducer, a 1.75D transducer, a 2D transducer, a 3D transducer, and so on. In some embodiments, the transducer array 302 can include one or more piezoelectric transducers. In some other embodiments, the transducer array 302 may include one or more capacitive micromachined ultrasonic transducers ("CMUTs").

When energized by a transmitter 306, a given transducer element 304 produces a burst of ultrasonic energy. The ultrasonic energy reflected back to the transducer array 302 (e.g., an echo) from the object or subject under study is converted to an electrical signal (e.g., an echo signal) by each transducer element 304 and can be applied separately to a receiver 308 through a set of switches 310. The transmitter 306, receiver 308, and switches 310 are operated under the control of a controller 312, which may include one or more processors. As one example, the controller 312 can include a computer system.

The transmitter 306 can be programmed to transmit unfocused or focused ultrasound waves. In some configurations, the transmitter 306 can also be programmed to transmit diverged waves, spherical waves, cylindrical waves, plane waves, or combinations thereof. Furthermore, the transmitter 306 can be programmed to transmit spatially or temporally encoded pulses.

The receiver 308 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 306 and the receiver 308 can be programmed to implement a high frame rate. For instance, a frame rate associated with an acquisition pulse repetition frequency ("PRF") of at least 100 Hz can be implemented. In some configurations, the ultrasound system 300 can sample and store at least one hundred ensembles of echo signals in the temporal direction.

The controller 312 can be programmed to implement the methods described in the present disclosure, such as by operating the ultrasound system 300 in a pulsed-wave or continuous Doppler mode to acquire ultrasound data from a region-of-interest containing a fluid-media interface or boundary layer. In some embodiments, the controller 312 receives user inputs defining various factors used in the design of the imaging sequence. For instance, the controller 312 can be programmed to dynamically change the operating frequency of the transducer elements 304 in order to dynamically adjust the pressure sensitivity of the ultrasound system 300.

A scan can be performed by setting the switches 310 to their transmit position, thereby directing the transmitter 306 to be turned on momentarily to energize transducer elements 304 during a single transmission event according to the selected imaging sequence. The switches 310 can then be set to their receive position and the subsequent echo signals produced by the transducer elements 304 in response to one or more detected echoes are measured and applied to the receiver 308. The separate echo signals from the transducer elements 304 can be combined in the receiver 308 to produce a single echo signal.

The echo signals are communicated to a processing unit 314, which may be implemented by a hardware processor and memory, to process echo signals or images generated from echo signals. As an example, the processing unit 314 can convert ultrasound data to pressure data using the methods described in the present disclosure. Images produced from the echo signals by the processing unit 314 can be displayed on a display system 316.

Figure 4:
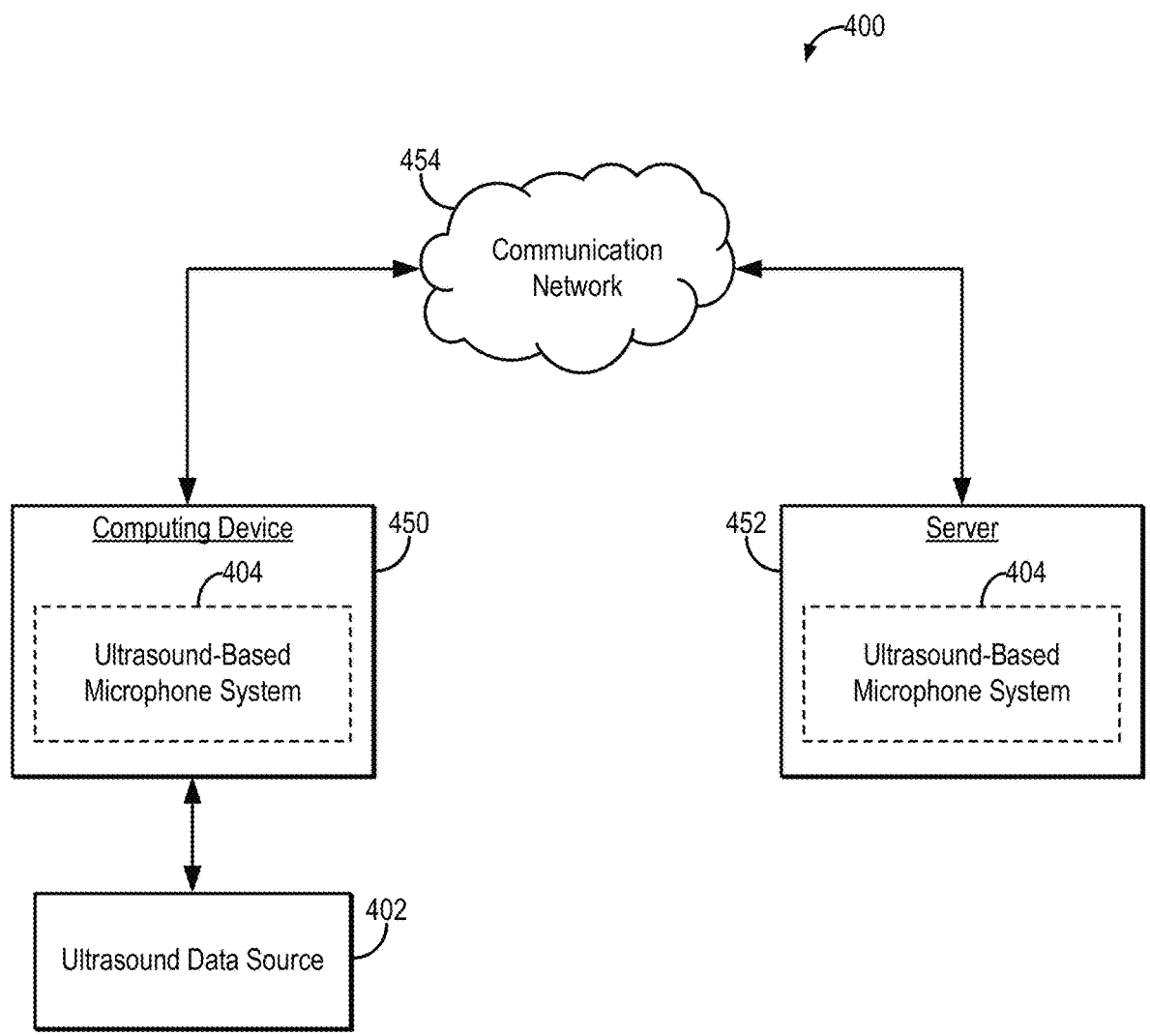
FIG. 4 is a block diagram of an example ultrasound-based microphone system that can implement the methods described in the present disclosure.

Referring now to FIG. 4, an example of a system 400 for measuring pressure or pressure variations at a fluid-media interface using ultrasound in accordance with some embodiments of the systems and methods described in the present disclosure is shown. As shown in FIG. 4, a computing device 450 can receive one or more types of data (e.g., ultrasound data) from ultrasound data source 402, which may be a Doppler signal spectra source. In some embodiments, computing device 450 can execute at least a portion of an ultrasound-based microphone system 404 to generate pressure and/or audio signal data from ultrasound data received from the ultrasound data source 402.

Additionally or alternatively, in some embodiments, the computing device 450 can communicate information about data received from the image source 402 to a server 452 over a communication network 454, which can execute at least a portion of the ultrasound-based microphone system 404. In such embodiments, the server 452 can return information to the computing device 450 (and/or any other suitable computing device) indicative of an output of the ultrasound-based microphone system 404.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, ultrasound data source 402 can be any suitable source of ultrasound data (e.g., measurement data, images reconstructed from measurement data), such as an ultrasound system, another computing device (e.g., a server storing ultrasound data), and so on. In some embodiments, ultrasound data source 402 can be local to computing device 450. For example, ultrasound data source 402 can be incorporated with computing device 450 (e.g., computing device 450 can be configured as part of a device for capturing, scanning, and/or storing images). As another example, ultrasound data source 402 can be connected to computing device 450 by a cable, a direct wireless link, and so on. Additionally or alternatively, in some embodiments, ultrasound data source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
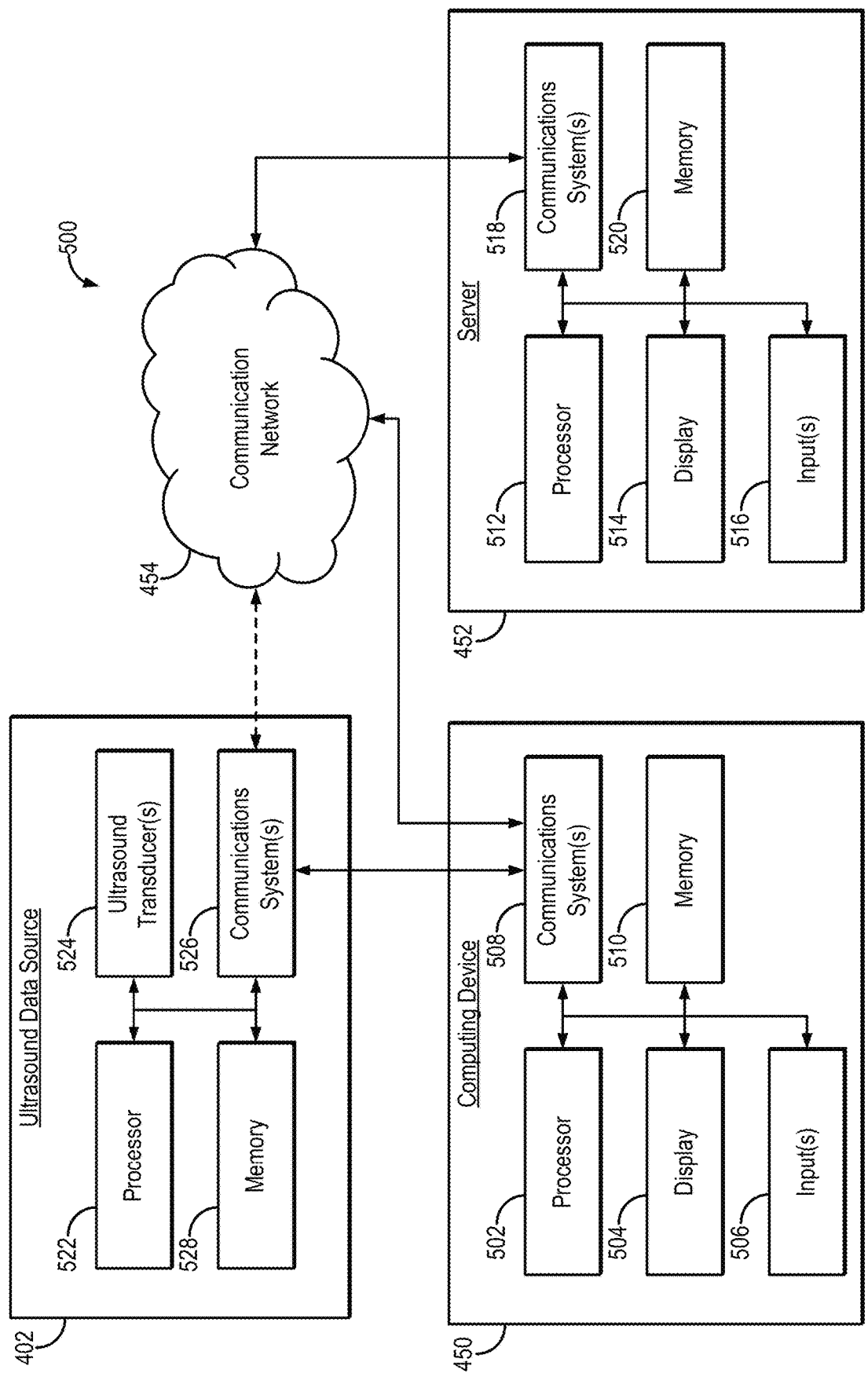
FIG. 5 is a block diagram of example components of the ultrasound-based microphone system of FIG. 4.

Referring now to FIG. 5, an example of hardware 500 that can be used to implement ultrasound data source 402, computing device 450, and server 454 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, ultrasound data source 402 can include a processor 522, one or more ultrasound transducer 524, one or more communications systems 526, and/or memory 528. In some embodiments, processor 522 can be any suitable hardware processor or combination of processors, such as a CPU, a GPU, and so on. In some embodiments, the one or more ultrasound transducers 524 are generally configured to acquire data, images, or both. Additionally or alternatively, in some embodiments, one or more ultrasound transducer 524 can include any suitable hardware, firmware, and/or software for coupling to and/or controlling operations of an ultrasound transducer or ultrasound system. In some embodiments, one or more portions of the one or more ultrasound transducer 524 can be removable and/or replaceable.

Note that, although not shown, ultrasound data source 402 can include any suitable inputs and/or outputs. For example, ultrasound data source 402 can include input devices and/or sensors that can be used to receive user input, such as a keyboard, a mouse, a touchscreen, a microphone, a trackpad, a trackball, and so on. As another example, ultrasound data source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more image acquisition systems 524, and/or receive data from the one or more image acquisition systems 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of image source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for measuring pressure using an ultrasound system, the method comprising:
   (a) acquiring ultrasound data from a region-of-interest containing an interface between a first medium and a second medium, wherein the ultrasound data are acquired using an ultrasound system by:
      generating with the ultrasound system one or more transmitted ultrasound waves directed towards the region-of-interest; and
      detecting one or more ultrasound waves reflected from the region-of-interest in response to the one or more transmitted ultrasound waves interacting with vibrations caused at the interface between the first medium and the second medium by displacements propagating in the first medium, wherein the one or more ultrasound waves reflected from the region-of-interest encode the vibrations caused at the interface by the displacements propagating in the first medium and wherein the one or more ultrasound waves reflected from the region-of-interest do not capture ambient and environmental noise in the region-of-interest;
   (b) accessing the ultrasound data with a computer system in order to process the ultrasound data, generating output as at least one of displacement or pressure data indicative of displacement or pressure measurements associated with the displacements propagating in the first medium; and
   (c) outputting the at least one of the displacement or pressure data to a user using the computer system, wherein the at least one of the displacement or pressure data have reduced noise based on the ambient and environmental noise not being captured in the ultrasound data.

2. The method as recited in claim 1, wherein the displacements propagating in the first medium correspond to one or more pressure waves propagating in the first medium.

3. The method as recited in claim 2, wherein the one or more pressure waves comprise one or more acoustic pressure waves.

4. The method as recited in claim 1, wherein the interface is a fluid-media interface that comprises an air-media interface.

5. The method as recited in claim 4, wherein the fluid-media interface is an air-media interface that comprises an interface between air and a tissue.

6. The method as recited in claim 5, wherein the tissue corresponds to at least one of a tracheal wall or a laryngeal wall.

7. The method as recited in claim 4, wherein the fluid-media interface is an air-media interface that comprises an interface between air and a non-biological material.

8. The method as recited in claim 7, wherein the non-biological material comprises at least one of a plastic, a metal, or a metallic alloy.

9. The method as recited in claim 1, wherein the one or more transmitted ultrasound waves are transmitted using a pulsed-wave Doppler mode of the ultrasound system.

10. The method as recited in claim 1, wherein the one or more transmitted ultrasound waves are transmitted using a continuous wave Doppler mode of the ultrasound system.

11. The method as recited in claim 1, wherein the at least one of displacement or pressure data are generated by comparing the ultrasound data to reference data indicative of a relationship between ultrasound data and pressure or displacement measurements.

12. The method as recited in claim 10, wherein the relationship is an empirically determined relationship.

13. The method as recited in claim 1, wherein the at least one of displacement or pressure data comprise pressure data that are generated by inputting the ultrasound data to a trained machine learning algorithm that has been trained to correlate ultrasound data with pressure measurements, generating output as the pressure data.

14. An ultrasound microphone, comprising:
an ultrasound transducer;
a controller in communication with the ultrasound transducer and programmed to:
  cause the ultrasound transducer to transmit one or more ultrasound waves;
  receive ultrasound data from the ultrasound transducer, the ultrasound data indicating an interaction between the one or more ultrasound waves and a fluid-media interface that is vibrating in response to one or more pressure waves propagating in the fluid;
  convert the ultrasound data to pressure data representative of pressure measurements associated with the one or more pressure waves propagating in the fluid; and
  dynamically change a pressure sensitivity by changing a frequency of the one or more ultrasound waves transmitted by the ultrasound transducer.

15. The ultrasound microphone as recited in claim 14, wherein the ultrasound transducer and the controller are arranged in a water-proof housing.

16. The ultrasound microphone as recited in claim 14, wherein the controller is programmed to cause the ultrasound transducer to transmit the one or more transmitted ultrasound waves using a pulsed-wave Doppler mode.

17. The ultrasound microphone as recited in claim 14, wherein the controller is programmed to cause the ultrasound transducer to transmit the one or more transmitted ultrasound waves using a continuous wave Doppler mode.

18. The ultrasound microphone as recited in claim 14, wherein the controller is programmed to convert the ultrasound data to the pressure or displacement data by comparing the ultrasound data to reference data indicative of a relationship between ultrasound data and pressure or displacement measurements.

* * * * *